United States Patent [19]

Misaki

[11] Patent Number: 4,693,971
[45] Date of Patent: Sep. 15, 1987

[54] HIGHLY SENSITIVE ENZYME ASSAY METHOD

[75] Inventor: Hideo Misaki, Shizuoka, Japan

[73] Assignee: Toyo Jozo Kabushiki Kaisha, Shizuoka, Japan

[21] Appl. No.: 575,292

[22] Filed: Jan. 30, 1984

[30] Foreign Application Priority Data

Jan. 28, 1983 [JP] Japan .................... 58-13057

[51] Int. Cl.$^4$ .............. C12Q 1/50; C12Q 1/44; C12Q 1/26; C12Q 1/32
[52] U.S. Cl. .......................... 435/17; 435/15; 435/19; 435/25; 435/26; 435/28
[58] Field of Search .............. 435/25, 26, 28, 15, 435/17, 18, 19

[56] References Cited

U.S. PATENT DOCUMENTS

| | | |
|---|---|---|
| 3,703,591 | 11/1972 | Bucolo et al. ............ 435/25 X |
| 4,223,090 | 9/1980 | Mazza ................... 435/25 X |
| 4,245,041 | 1/1981 | Denney ................. 435/19 X |
| 4,275,161 | 6/1981 | Misaki et al. ............ 435/822 |
| 4,399,218 | 8/1983 | Gauhl et al. ............. 435/25 |
| 4,446,231 | 5/1984 | Self ..................... 435/21 X |
| 4,492,751 | 1/1985 | Boguslaski et al. ........ 436/817 X |
| 4,547,461 | 10/1985 | Esders et al. ............ 435/25 X |
| 4,598,042 | 7/1986 | Self ..................... 435/26 X |

FOREIGN PATENT DOCUMENTS 2025426  1/1980  United Kingdom ............ 435/25

OTHER PUBLICATIONS

Mahler et al. (1971) *Biological Chemistry* 2nd Ed. p. 30.
Enzyme Nomenclature (1975) Elsevier Sci. Publ. Co., pp. 100–101.

Primary Examiner—Robert J. Warden
Assistant Examiner—Randall E. Deck
Attorney, Agent, or Firm—Young & Thompson

[57] ABSTRACT

A highly sensitive quantitative assay method for any one component which is L-glycero-3-phosphate (G3P), dihydroxyacetone-3-phosphate (DHAP), nicotinamide adenine dinucleotide (NAD) or reduced NAD, in a specimen to be assayed, comprising causing this component in the specimen to take part in the cycling reaction

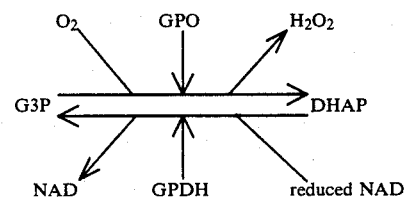

wherein GPO is glycerophosphate oxidase and GPDH is glycerophosphate dehydrogenase, and measuring a detectable change in the reaction system. There is thus provided a novel G3P-GHAP cycling reaction using GPO, which consumes $O_2$ and generates $H_2O_2$ and DHAP, with a substrate of G3P, and furthermore GPDH which consumes reduced NAD and generates NAD and G3P, with a substrate of DHAP. Examples of specimens are specimens which contain any one of G3P, DHAP, NAD or reduced NAD, or which liberate or generate such a component. By proceeding at a rate of more than ten cycles per minute and measuring the amount of a detectable change in the reaction, the component in a specimen can easily and sensitively be detected with good accuracy.

12 Claims, 9 Drawing Figures

HIGHLY SENSITIVE ENZYME ASSAY METHOD

This invention relates to a quantitative assay method for any one component, in a specimen to be assayed, which component can be L-glycero-3-phosphate (G3P), dihydroxyacetone-3-phosphate (DHAP), nicotinamide adenine dinucleotide (NAD) or reduced NAD. More particularly the present invention relates to a highly sensitive enzyme assay method which comprises reacting a component in the specimen with a component of the cycling reaction [I]

wherein GPO is glycerophosphate oxidase and GPDH is glycerophosphate dehydrogenase, and measuring the amount of a detectable change in the reaction system.

Heretofore, enzymatic cycling assay methods such as NAD cycling, NADP cycling or CoA cycling have been known. For example, alcohol dehydrogenase has been subjected to reaction with ethanol as a substrate in the presence of NAD to form reduced NAD which is oxidized to NAD by the action of malic dehydrogenase on a substrate of oxalacetate to constitute an NAD-reduced NAD cycling reaction. [Japan. Biochem. Soc. Ed. "Experimental Methods in Biochemistry", vol. 5, "Research Methods in Enzymology" p. 121-135, Tokyo Kagaku Dojin Publishing Co., Aug. 1975, Mori, A. Ed. "Manual of Assay Methods in Neuro-transmittance", p. 165-172, Ishiyaku Publishing Co., November, 1979.]

Another method has been known as follows:

In the above reaction, malic dehydrogenase is replaced by reduced NAD oxidase to constitute a cycling reaction wherein oxygen and reduced NAD are consumed and $H_2O$ and NAD are generated [Institute for Phys. and Chem. Sci. Ed.: "Present and Future of Life-Science", p. 30-32, K. K. Creative Life Sci. Res. Assn., March, 1981.] Hydroxysteroid is treated with hydroxysteroid dehydrogenase to reduce NAD to reduced NAD which is converted to NAD with the formation of formazane by the action of a transferase such as diaphorase in the presence of a tetrazolium salt to constitute the cycling reaction [Japan. Pat. Unexam. Publ., No. 56-144096.] Glutathione and dehydroascorbate are treated with glutathione dehydroascorbate oxidoreductase, thereby converting dehydroascorbate to ascorbate, which consumes oxygen and generates $H_2O$ and dehydroascorbate by the action of ascorbate oxidase to constitute a cycling reaction. [Japan. Pat. Unexam. Publ. No. 56-151498.] NAD cycling wherein consuming oxygen and generating hydrogen peroxide by using reduced NAD oxidase is also known [Japan. Pat. Unexam. Publ. No. 56-78599].

I have now discovered a G3P-GHAP cycling reaction using GPO, which consumes $O_2$ and generates $H_2O_2$ and DHAP, with a substrate of G3P, and furthermore GPDH which consumes reduced NAD and generates NAD and G3P, with a substrate of DHAP. These reagents can be provided at low cost and good quality, and moreover an effective cycling reaction can be achieved in spite of coexisting oxidatively active $H_2O_2$ and reductively active reduced NAD. Furthermore, I have found that in the cycling reaction, any one of the components to be assayed in a specimen containing any of G3P, DHAP, NAD, or reduced NAD, is reacted with the remainder of another component thereof, and that, by proceeding at a rate of more than ten cycles per minute and measuring the amount of a detectable change in the reaction, the component in a specimen can easily and sensitively be detected with good accuracy.

An object of the present invention is to provide, in an assay method for any one of component in a specimen to be assayed, which component can be G3P, DHAP, NAD or reduced NAD, a novel highly sensitive enzyme assay method.

This object is achieved, according to the present invention, by the method which I have now discovered, which comprises reacting a component in the specimen with a component of cycling reaction [I]

and measuring the amount of a detectable change in the reaction system.

Examples of specimens are specimens which contain any one of G3P, DHAP, NAD or reduced NAD, or which liberate or generate such a component. In the latter case, assaying enzymatic activity or the amount of substrate in various enzymatic reactions can be mentioned. Examples thereof are illustrated hereinbelow.

Enzymatic reaction systems which liberate or generate G3P are exemplified as follows:

(1) As a reaction system for assaying phosphatidyl glycerol in amniotic fluid for the examination of respiratory function of a fetus at full term:

A specimen containing phosphatidyl glycerol (PG) such as amniotic fluid is treated with phospholipase C (EC 3.1.4.3) to liberate diglyceride and G3P, and the G3P is assayed.

(2) As an assay system for G3P liberated by an enzymatic reaction system of ATP, glycerol and glycerokinase (GK, EC 2.7.1.30) wherein ATP or glycerol, or glycerokinase activity, is assayed:

(3) In the above reaction system (2), the glycerol is derived from the enzymatic reaction of PG and phospholipase D (EC 3.1.4.4), and PG or phospholipase activity is assayed:

(4) In the above reaction system (2), the glycerol is derived from the enzymatic reaction of mono-, di- or tri-glyceride and lipase (EC 3.1.1.3), wherein a glyceride such as triglyceride in serum or lipase such as pancreatic lipase in serum is assayed:

(n = 1 in monoglyceride, n = 2 in diglyceride, n = 3 in triglyceride)

(5) In the above reaction system (2), the ATP is derived from an enzymatic reaction system of creatine phosphate, ADP and creatine kinase (CK, EC 2.7.3.2), wherein creatine phosphate is measured or creatine kinase (CK) activity is assayed:

(6) In the above reaction system (2), the ATP is derived from an enzymatic reaction system of phosphoenol pyruvate, ADP and pyruvate kinase (PK, EC 2.7.1.40), wherein phosphoenol pyruvate is measured or pyruvate kinase activity is assayed:

(7) In the above reaction system (2), the reaction system for ATP wherein the ATP is derived from an enzymatic reaction system of acetylphosphate, ADP and acetate kinase (EC 2.7.2.1) is as follows:

(8) In the above reaction system (2), the reaction system for ATP wherein the ATP is derived from an enzymatic reaction system of 4-phospho-L-aspartate, ADP and aspartate kinase (Asp K, EC 2.7.2.4) is as follows:

(9) In the above reaction system (2), the reaction system for ATP, wherein the ATP is derived from arginine phosphate, ADP and arginine kinase (Arg K, EC 2.7.3.3) is as follows:

An enzymatic reaction system which liberates or generates DHAP is illustrated as follows:

(10) A reaction system for measuring keto-1-phosphate or assaying aldorase activity by assaying DHAP which is liberated or generated by an enzymatic reaction system of ketose-1-phosphate (K-1-P) and aldorase (EC 4.1.2.7):

(11) A reaction system for measuring D-glyceroaldehyde-3-phosphate or assaying triosephosphate isomerase by assaying DHAP which is liberated or generated by an enzymatic reaction system of D-glyceroaldehyde-3-phosphate and triphosphateisomerase (TPI, EC 5.3.1.1):

Furthermore, an enzymatic reaction system which liberates or generates reduced NAD is illustrated hereinbelow.

In this reaction system, remaining unreacted NAD should be decomposed under alkaline conditions such as at above pH 12 at 10° C. for 10 minutes after the reaction is complete.

(12) A reaction system for measuring ethanol or assaying alcohol dehydrogenase activity by assaying reduced NAD which is liberated or generated by an enzymatic reaction system of ethanol, NAD and alcohol dehydrogenase (ADH, EC 1.1.1.1):

(13) A reaction system for measuring 3-α-hydroxysteroid in bile acids or assaying 3-α-hydroxysteroid dehydrogenase by assaying reduced NAD which is liberated or generated from an enzymatic reaction system of 3-α-hydroxysteroid, NAD and 3-α-hydroxysteroid dehydrogenase (HSDH, EC 1.1.1.50):

3-ketosteroid + reduced NAD (14) A reaction system for measuring L-lactate or assaying lactate dehydrogenase activity by assaying reduced NAD which is liberated or generated from an enzymatic reaction system of L-lactate, NAD and lactate dehydrogenase (LDH, EC 1.1.1.27):

(15) A reaction system for measuring glucose or assaying glucose dehydrogenase activity by assaying reduced NAD which is liberated or generated from an enzymatic reaction system of glucose, NAD and glucose dehydrogenase (DGH, EC 1.1.1.47):

Furthermore, an enzymatic reaction system which liberates or generates NAD is illustrated hereinbelow. In this reaction system, remaining unreacted reduced NAD should be decomposed at below pH 2 at 50° C. for over 3 minutes after the reaction is complete, and then neutralized for NAD assay.

(16) A reaction system for measuring proline or assaying D-proline reductase by assaying NAD which is liberated or generated from an enzymatic reaction system of proline, reduced NAD and D-proline reductase (PR, EC 1.4.1.6):

(17) A reaction system for measuring L-cystine or assaying cystine reductase activity by assaying NAD which is liberated or generated from an enzymatic reaction system of L-cystine, reduced NAD and cystine reductase (CR) (EC 1.6.4.1):

The above enzymatic reaction systems are illustrative only, and to the specimen to be assayed can be added further one or more other reaction systems which can liberate or generate any one of the components of the reaction systems hereinabove.

To a specimen containing any one of the components to be assayed in these enzymatic reaction systems are added the reagents necessary for producing the enzymatic reaction system. The reaction mixture can be a specimen containing any one of components G3P, DHAP, NAD or reduced NAD. These enzymatic reaction systems can be prepared and processed individually or simultaneously according to cycling reaction [I].

The amount of the specimen can be 0.05–10 ml and the reaction proceeds by mixing the specimen with a weakly acidic to weakly alkaline buffer solution containing the required reagents, at 30° C. for generally more than one minute. The amount of reagents to be added is not limited but is generally in stoichiometric excess as compared with the component to be assayed.

In reaction [I], one mole of G3P is converted with the consumption of one mole of $O_2$, generally dissolved oxygen, to one mole of DHAP with the generation of one mole of $H_2O_2$ by the action of GPO [GPO: refer to U.S. Pat. No. 4,275,161] to constitute the GPO reaction system. Then one mole of DHAP is further converted by the action of GPDH (EC 1.1.1.8) in the presence of one mole of reduced NAD to one mole of G3P with the generation of one mole of NAD, to constitute the GPDH reaction system. Furthermore the thus-generated G3P is converted to DHAP to constitute the GPO reaction system, thereby constituting the cycling reaction. The said cycling reaction [I] proceeds in the presence of the six components G3P, DHAP, GPO, GPDH, reduced NAD and $O_2$; however, G3P and DHAP can be formed from each other by a cycling reaction, and therefore either one thereof can be used as desired.

Furthermore, in the cycling reaction [I], $H_2O_2$ and reduced NAD can be linked to form NAD, wherein one mole of $H_2O_2$ and one mole of reduced NAD are consumed to form two moles of $H_2O$ and one mole of NAD by the action of NAD peroxidase (EC 1.11.1.1) [*J. Biol. Chem.*, 225: 557, 1957] as shown by reaction [II]

In cycling reaction [II], $H_2O_2$ generated in cycling reaction [I] is consumed with reduced NAD to form NAD, and so two moles of reduced NAD are consumed in one cycle of cycling reaction [II], which provides twofold more rapid changes in the amount of reduced NAD and a more highly sensitive assay method.

Alternatively, NAD can be converted by another dehydrogenase (herein called a second dehydrogenase) and its substrate to reduced NAD to constitute an NAD cycling reaction consisting of NAD, the second dehydrogenase and the substrate thereof. The said NAD cycling can be linked with cycling reaction [I] as illustrated by reaction [III].

For example, a component in the specimen (shown as ➡) and a component which constitutes cycling reaction [I] (shown as ▭) can be illustrated as follows:

(a) Component in specimen: G3P:

In the cycling reaction [Ia], wherein the component in the specimen is G3P, then GPO, GPDH, $O_2$ and reduced NAD are used for the components which constitute the cycling reaction. GPO catalyzes a reaction, in which G3P is the substrate, which consumes one mole of G3P and $O_2$ and generates one mole of $H_2O_2$ and DHAP. Furthermore, GPDH acts on a substrate of DHAP to consume one mole of DHAP and reduced NAD and generate one mole of G3P and NAD, thereby to complete the G3P-DHAP cycling reaction. In the reaction, $O_2$ can be supplied by dissolved oxygen in the system and so GPO, GPDH and reduced NAD should be supplied in excess amounts as reagents for the assay. The amount of G3P in the specimen is not limited and is naturally diluted at high concentration. The amount of GPO and GPDH depends on the amount of G3P in the specimen and is usually more than 0.1 unit per one test, preferably 2–50 units for GPO and 0.5–40 units for GPDH. The amount of reduced NAD can be more than the product of the amount of G3P in the specimen times the number of cycles, and is generally in stoichiometric excess of the amount of G3P, for example more than 50 times, preferably 100–1000 times. The magnitude of the detectable change after the cycling reaction is completed can be determined by the amount of consumed $O_2$ or reduced NAD or generated $H_2O_2$. As shown in cycling reaction [II] hereinbefore, the generated $H_2O_2$ and consumed reduced NAD can be linked for highly sensitive assaying. In this linked reaction, NAD peroxidase is used, in general, in an amount more than 0.5 unit per one test, preferably 1–20 units. The magnitude of the detectable change can preferably be determined by measuring the consumed reduced NAD.

(b) Component in specimen: DHAP:

The schema is illustrated in reaction [Ib]

[Ib]

Any of GPO, GPDH, $O_2$ and reduced NAD can be the component which completes the cycling reaction [Ib]. In this reaction, DHAP-G3P cycling is characterized by consuming one mole of DHAP and reduced NAD to generate one mole of NAD and G3P, then by consuming one mole of G3P and $O_2$ to generate one mole of $H_2O_2$ and DHAP. $O_2$ can be supplied by dissolved oxygen and so GPO, GPDH and reduced NAD are simply added in stoichiometric excess. The amount of GPDH and of GPO is generally more than 0.1 unit, preferably 5–40 units for GPDH and 1–50 units for GPO. The amount of reduced NAD to be used is determined by the product of the amount of DHAP in the specimen times the number of cycles, and is in general, in stoichiometric excess as compared with the amount of DHAP, for example more than 50 times, preferably 100–1000 times. The magnitude of the detectable change after completion of the cycling reaction can be determined by consumed oxygen or reduced NAD or generated $H_2O_2$. High sensitivity of assay can be achieved by using NAD peroxidase as hereinbefore illustrated.

(c) Component in specimen: reduced NAD:

The cycling reaction can be illustrated by reaction [Ic]

[Ic]

In this reaction, DHAP, GPO, GPDH, the second dehydrogenase, the substrate for the second dehydrogenase, or $O_2$ can be used as the component completing the cycling reaction [Ic], and one mole of reduced NAD and DHAP is consumed to form one mole of NAD and G3P by the action of GPDH on reduced NAD. Furthermore, GPO acts on G3P by consuming one mole of G3P and $O_2$ to form one mole of $H_2O_2$ and DHAP. Then the DHAP-G3P cycling reaction can be completed. Simultaneously, the NAD formed from reduced NAD by the action of GPDH is converted, with an equimolar ratio of substrate for the second dehydrogenase, to one molar ratio of reduced NAD and the oxidative product by the action of the second dehydrogenase. The said reduced NAD is thereby used in the DHAP-G3P cycling reaction. $O_2$ can be supplied from dissolved oxygen in the system, and DHAP, GPO, GPDH, the second dehydrogenase and the substrate therefor can be added in stoichiometric excess.

The magnitude of the detectable change can be determined by measuring consumed $O_2$ and reduced NAD and generated $H_2O_2$.

(d) Component in specimen: NAD:

The cycling reaction is illustrated by reaction [Id]

[Id]

DHAP, GPO, GPDH, $O_2$, the second dehydrogenase and the substrate for the second dehydrogenase are used as the components which complete the cycling reaction [Id]. In this reaction, the second dehydrogenase acts on NAD, and one mole of NAD and the substrate for the second dehydrogenase is consumed to generate one mole of oxidative product and reduced NAD, then the reduced NAD is used in the DHAP- G3P cycling reaction. The GPDH acts on the generated reduced NAD and an equimolar ratio of DHAP to generate one mole of NAD and G3P, and then one mole of G3P and O₂ are consumed by the action of GPO to form one mole of H₂O₂ and DHAP. In this reaction, O₂ can be supplied from dissolved oxygen in the mixture, and so DHAP, GPO, GPDH, the second dehydrogenase and its substrate should be supplied as reagents for assaying in excess amounts. The magnitude of the detectable change can be determined by measuring consumed O₂ or generated H₂O₂.

The second dehydrogenase used in the cycling reactions [Ic] and [Id] can be an enzyme which catalyzes a reaction on a substrate for the said dehydrogenase and NAD to form oxidative products of the said substrate and reduced NAD, and is illustrated hereinbelow.

(18) Dehydrogenase; D-arabitol dehydrogenase (A Dase) (EC 1.1. 1.11) and its substrate: D-arabitol:

D—arabitol + NAD $\xrightarrow{\text{A Dase}}$ D—xylose + reduced NAD (19) Lactate dehydrogenase (LDH) (EC 1.1.1.27) and L-lactate:

L—lactate + NAD $\xrightarrow{\text{LDH}}$ pyruvate + reduced NAD (20) Malate dehydrogenase (decarboxylating) (MDH) (EC 1.1.1.28) and L-malate:

L—malate + NAD $\xrightarrow{\text{MDH}}$ pyruvate + CO₂ + reduced NAD (21) Glucose dehydrogenase (GDH) (EC 1.1.1.47) and glucose:

β-D—glucose + NAD $\xrightarrow{\text{GDH}}$ D—glucono-δ-lactone + reduced NAD (22) 3-α-hydroxysteroid dehydrogenase (α-HSDH) (EC 1.1.1.50) and 3-α-steroid such as androsterone and cholate:

3-α-hydroxysteroid + NAD $\xrightarrow{\text{α-HSDH}}$ 3-ketosteroid + reduced NAD (23) Formate dehydrogenase (FDH) (EC 1.2.1.2) and formate:

formate + NAD $\xrightarrow{\text{FDH}}$ CO₂ + reduced NAD (24) Galactose dehydrogenase (Gal DH) (EC 1.1.1.48) and D-galactose:

D—galactose $\xrightarrow{\text{Gal DH}}$ D—galactose-γ-lactone + reduced NAD (25) β-hydroxysteroid dehydrogenase (β-HSDH) (EC 1.1.1.51) and 3-β-hydroxysteroid:

3-β-hydroxysteroid + NAD $\xrightarrow{\text{β-HSDH}}$ 3-ketosteroid + reduced NAD In cycling reaction [Id], NAD in the specimen is converted to reduced NAD by the action of the second dehydrogenase in the presence of a substrate therefor to take part in the NAD cycling reaction, then the thus-generated reduced NAD participates in the same cycling reaction as in [Ic] hereinbefore.

The amount of reagents used in cycling reactions [Ic] and [Id] can be in stoichiometric excess of the amount of NAD or reduced NAD. Furthermore, the said NAD cycling reaction can be linked by the action of NAD peroxidase as illustrated in cycling reaction [II].

Then any one of the components G3P, DHAP, NAD or reduced NAD in the specimen or a specimen which liberates or generates the said component is measured and the said component or specimen can be assayed based on the above cycling reaction [Ia], [Ib], [Ic] or [Id]. In the reaction, the number of cycles is more than 10, and so the amount of reagents used is preferably in molar excess of the number of cycles. Furthermore, trace amounts of specimen or diluted specimen are advantageously used.

The reaction medium can be a stable pH buffer solution, generally weakly acidic to weakly alkaline. For example, a phosphate buffer of pH 6.5–8.5, a tris-HCl buffer, an imidazole-HCl buffer, a dimethylglutarate-NaOH buffer or a PIPES-NaOH buffer can be used. The reaction proceeds generally at 37° C. for more than one minute.

Cycling reaction [I] proceeds usually at a rate of more than 50 cycles per minute, although this value varies depending on the amount of enzyme used or its Km value, and so the amount of enzyme and reagents can be provided preferably for more than 80 cycles/min. of reaction.

Next, the magnitude of a detectable change in the reaction is measured after the reaction proceeds, and the said detectable change is the quantity a component, which consumes or generates one molar ratio of the component, in one reaction cycle wherein one mole of G3P or DHAP is consumed or generated during cycling reaction [I]. The preferred component to be measured is consumed O₂ or reduced NAD, or generated H₂O₂.

The amount of consumed O₂ can usually be determined by the value of electro-chemical changes using an oxygen electrode. The amount of consumed reduced NAD can be determined by subtracting the amount of reduced NAD remaining at the end of the reaction from the initial amount of reduced NAD. Measuring these amounts of reduced NAD can be done by various known assay methods. For example, the specific absorbency of reduced NAD and the nonspecific absorbency of NAD can be measured. Since NAD has its specific absorption maximum at 260 nm and reduced NAD at 260 nm and 340 nm, the absorbency at 320–360 nm, preferably at 340 nm is measured for assaying reduced NAD.

Another assay method for reduced NAD is a colorimetric assay using an electron transport chromogen having an electron acceptor from reduced NAD. Examples of electron transport chromogens are tetrazolium salts such as 3-(p-iodophenyl)-2-(p-nitrophenyl)-5- phenyl-2H-tetrazolium chloride, 3-(4,5-dimethyl-2-thiazolyl)-2,5-diphenyl-2H-tetrazolium bromide, 3,3'-(4,4'-biphenylene)-bis 2,5-diphenyl-2H-tetrazolium chloride), 3,3'-(3,3'-dimethoxy-4,4'-biphenylene)-bis [2-(p-nitrophenyl)-5-phenyl-2H-tetrazolium chloride] (=nitro-tetrazolium: NTB), 3,3'-(3,3'-dimethoxy-4,4'biphenylene)-bis [2,5-bis (p-nitrophenyl)-2H-tetrazolium chloride], 3,3'-(3,3'-dimethoxy-4,4'-biphenylene)-bis (2,5-diphenyl-2H-tetrazolium chloride), and 2,6-dichlorophenol-indophenol. A preferred example is a combination of a water-soluble tetrazolium salt and diaphorase or phenazinemethosulfate. These electron transport chromogens are electron acceptors for reduced NAD to form a colored formazane pigment, and the thus-formed pigment is colorimetrically measured at the maximum absorption thereof such as 500–550 nm.

A further assay method for reduced NAD is fluorometry wherein reduced NAD is treated with diaphorase in the presence of a fluorescent reagent such as resazulin. For assaying reduced NAD in cycling reaction [I], $H_2O_2$ should preferably be decomposed and removed by catalase. NAD peroxidase (EC 1.11.1.1) can be added to cycling reaction [I] for a doubly sensitive assay as illustrated in reaction system [II] hereinbefore. Generated $H_2O_2$ can be measured as an electro-chemical change by using a hydrogen peroxide electrode, or as a detectable product by reacting with an indicator and $H_2O_2$. Examples of indicators are reagents which can be measured by spectrophotometric means, color indicators, fluorescent reagents or luminescent reagents.

The present invention is thus a novel assay method using a G3P-DHAP cycling reaction at a rate of more than 10 cycles per minute, wherein a component in a specimen can be measured with good accuracy and high sensitivity.

The following examples illustrate the present invention but are not to be construed as limiting.

The results of the examples are shown in the accompanying drawings, in which.

EXAMPLE 1

Reaction mixture (1.0 ml):
50 mM phosphate buffer (pH 7.5)
10 mM glycerol
10 mM $MgCl_2$
glycerokinase (Toyo Jozo Co., produced from Streptomyces): 2 units/test
GPO (Toyo Jozo Co., produced from Aerococcus): 20 units/test
0.25 mM reduced NAD
GPDH (commercial product: rabbit muscle): 8 units/test The above reaction mixture (1.0 ml) was introduced into a quartz cell (1.0 ml) and was set in a spectrophotometer assembled with a constant temperature cell-holder set at 37° C.

Figure 1:
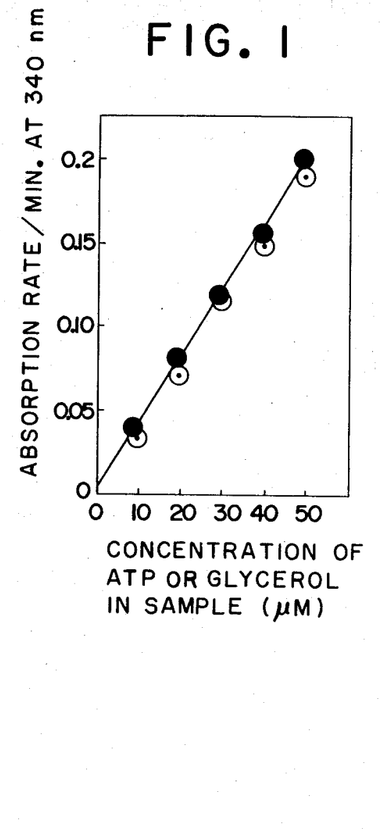
FIG. 1 is the quantitative assay curve for ATP or glycerol.

Specimens containing ATP (0, 10, 20, 30, 40 and 50 μM, respectively) (20 μl) were added thereto and each mixture was incubated at 37° C. Changes of absorbency each 2 minutes from 3 to 5 minutes after starting the reaction were measured at 340 nm. The results are shown in FIG. 1 ( ) with high sensitivity of assay.

In the above reaction mixture, glycerol is replaced by 5 mM ATP, and solutions containing trace amounts of glycerol (0, 10, 20, 30, 40 and 50 μM, respectively) were incubated and measured under the same conditions as hereinabove. The results are shown in FIG. 1 ( ), in which a good quantitative results was obtained.

Control measurements were carried out by adding specimens (20 μl) containing ATP (0, 0.5, 1.0, 2.0, 4.0, 6.0 and 10.0 mM, respectively) to aliquots of a reaction mixture (3 ml) each containing 50 mM phosphate buffer (pH 8.0), 10 mM glycerol, 10 mM $MgCl_2$, glycerokinase (2 units/text), GPO (5 units/test), 1.5 mM 4-aminoantipyrine, 1.5 mM phenol, peroxidase (5 units/test) and 0.1% Triton X-100, incubating the mixtures at 37° C. for 10 minutes and colorimetrically measuring them at 500 nm. The results are shown in FIG. 2.

Figure 2:
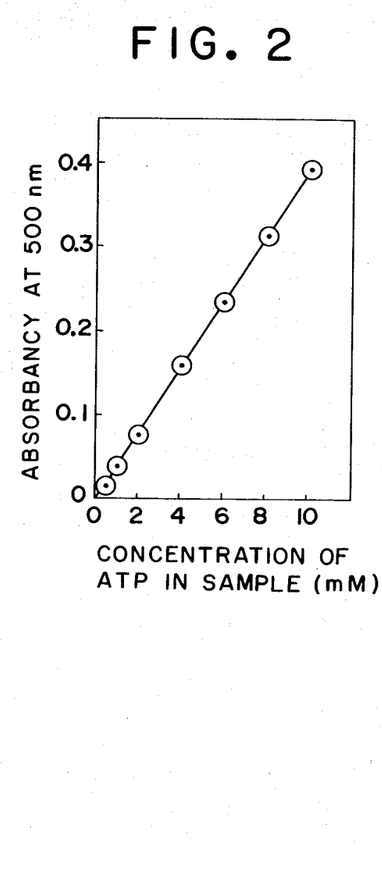
FIG. 2 is the quantitative assay curve for ATP using a non-cycling reaction.

Comparing with the results of a non-cycling reaction for ATP as shown in FIG. 2, the cycling reaction of the present invention, at a rate of approximately 35 cycles/min., is about 2000 times more sensitive as to assay after one hour's reaction, as compared with the control assay shown in FIG. 2.

EXAMPLE 2

Reaction mixture (1.0 ml):
50 mM phosphate buffer (pH 7.5)
GPO (20 units/test)
0.25 mM reduced NAD
GPDH (8 units/test)

Figure 3:
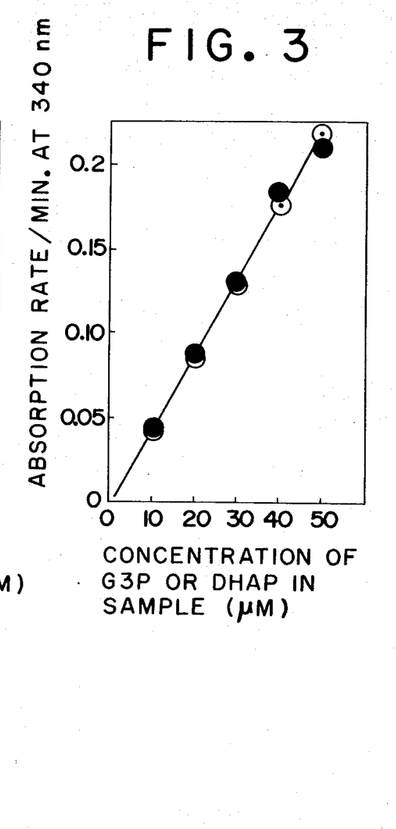
FIG. 3 is the quantitative assay curve for G3P or DHAP.

The above reaction mixture (1.0 ml) was introduced into a quartz cell (1.0 ml) and preincubated at 37° C. Specimens (20 μl) containing G3P (0, 10, 20, 30, 40 and 50 mM, respectively) were added thereto. The changes of absorbency at 340 nm at 2 minute time intervals beginning 3 minutes after starting the incubation were measured and the changes of absorbency per minute were calculated. The results are shown in FIG. 3. ( ). The specimens containing G3P were replaced by specimens containing DHAP (0, 10, 20, 30, 40 and 50 nm, respectively) and the material was incubated and measured in the same way as illustrated hereinabove. The results are shown in FIG. 3. ( ).

As illustrated, trace amounts of G3P or DHAP can be assayed.

EXAMPLE 3

NAD peroxidase (3 units/ml) [from Streptococcus; Colin et al., *J. Biol. Chem.*, 225: 557,1957] was added to the reaction mixture in Example 2 to prepare the reaction mixture (1.0 ml).

Specimens (20 μl) containing G3P (0, 5, 10, 15, 20 and 25 μM, respectively) were added to the said reaction mixture (1.0 ml) and the mixture was incubated at 37° C. The absorbency at 2-minute intervals beginning 3 minutes after the reaction started was measured at 340 nm.

Figure 4:
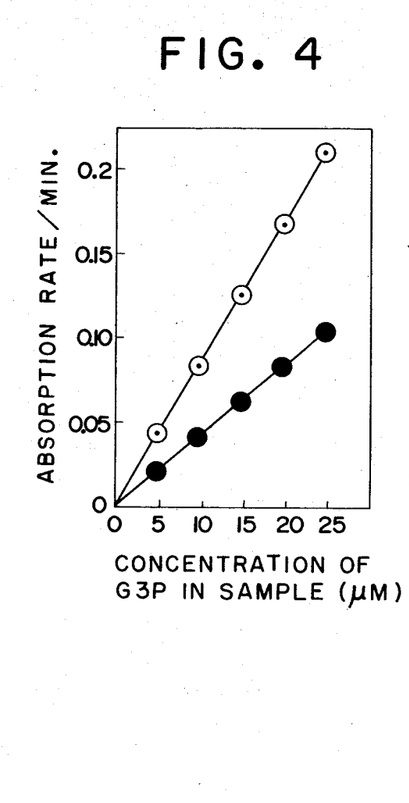
FIG. 4 is the quantitative assay curve for G3P using NAD peroxidase.

The results are shown in FIG. 4. In FIG. 4, : NAD peroxidase is used, : no NAD peroxidase is used. As shown in FIG. 4, doubly sensitive results can be obtained by using NAD peroxidase.

EXAMPLE 4

Reaction mixture (1.0 ml):
50 mM phosphate buffer (pH 7.5)
10 mM glycerol
10 mM $MgCl_2$
glycerokinase (2 units/test)
GPO (2.0 units/test)
0.25 mM reduced NAD
GPDH (8 units/test)

The above reaction mixture (1.0 ml) was introduced into the reaction vessel at a constant temperature of 37° C., and the temperature of the reaction mixture was maintained uniform by mixing with a magnetic stirrer.

Figure 5:
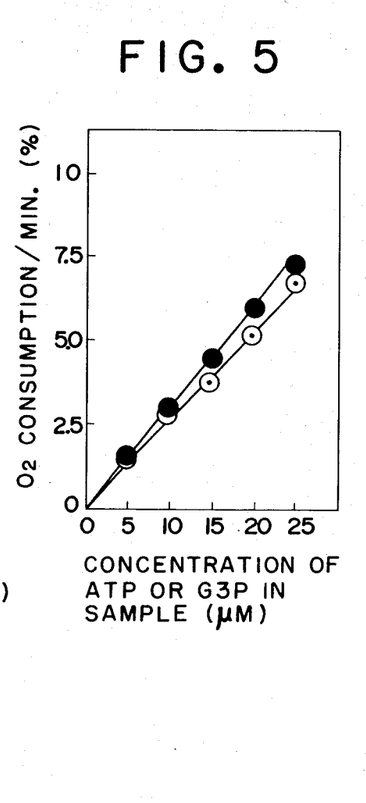
FIG. 5 is the quantitative assay curve for ATP or G3P using an oxygen electrode.

Specimens containing ATP (0, 5, 10, 15, 20 and 25 M, respectively) were added thereto, and the oxygen consumption ratio in the incubation reaction was measured by a Galvani-type oxygen electrode. The results are shown in FIG. 5 ( ) [$O_2$ consumption/min. (%)]. ATP was replaced by G3P, and specimens (20 μl) containing G3P (0, 5, 10, 15, 20 and 25 M, respectively) were used for incubation. The results are shown in FIG. 5 ( ). As a result, ATP and G3P can easily be assayed with good accuracy and high sensitivity.

EXAMPLE 5

Figure 6:
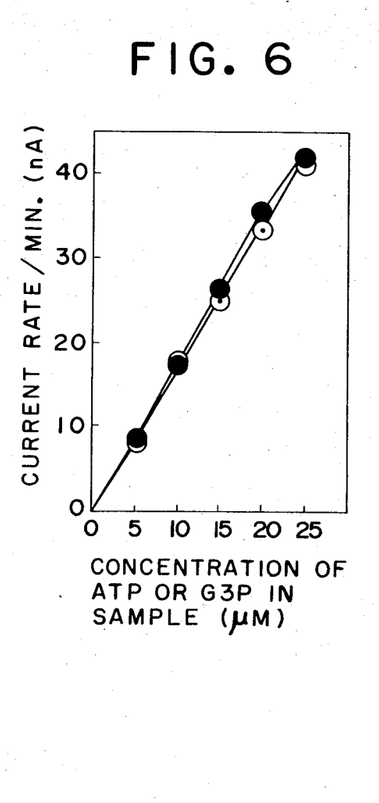
FIG. 6 is the quantitative assay curve for ATP or G3P using a hydrogen peroxide electrode.
Figure 7:
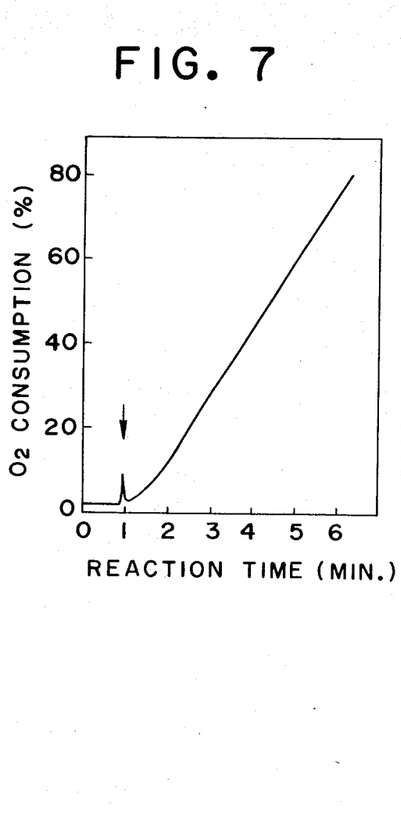
FIG. 7 is the quantitative assay curve for creatine kinase.

A reaction mixture (1.0 ml) having the same composition as in Example 4 was used, and the amount of $H_2O_2$ generated during the reaction was measured by a hydrogen peroxide electrode as electric current changes (nA) per minute.

The results are shown in FIG. 6. In FIG. 6: : $H_2O_2$ quantitative assay curve using specimens containing ATP (0–25 μM, 20 μl), and : G3P specimens (0–25 μM, 20 μl). Hydrogen peroxide electrode: YSI Co., Model 25 oxidative meter Clark 2510 oxidase probe.

EXAMPLE 6

Reaction mixtures for assaying creatine kinase:
Reaction mixture I:
50 mM phosphate buffer (pH 7.5)
40 mM creatine phosphate
5 mM β-mercaptoethanal
3 mM ADP
10 mM $MgCl_2$
glycerokinase (one unit/test)
Reaction mixture II:
GPO (15 units/test)
0.3 mM reduced NAD
GPDH (8 units/test)

The above reaction mixture I (0.2 ml) was introduced into a small test tube and preincubated at 37° C. Creatine kinase 10 μl) (Boehringer: rabbit muscle, 0.01 unit/ml) was added thereto, and the mixture was incubated for 10 minutes. The reaction was stopped by heating at 100° C. for 2 minutes. Reaction mixture II (0.8 ml) (preincubated at 37° C.) was added thereto, then the oxygen consumption after starting the reaction was measured by an oxygen electrode.

EXAMPLE 7

Reaction mixtures for phosphatidyl glycerol assay:
Reaction mixture I:
20 mM collidine buffer (pH 8.0)
phospholipase C (20 units/test)
10 mM $CaCl_2$
0.1% sodium deoxycholate
Reaction mixture II:
50 mM Tris-HCl buffer (pH 7.5)
GPO (15 units/test)
catalase (200 units/test)
0.25 mM reduced NAD
GPDH (8 units/test)

Figure 8:
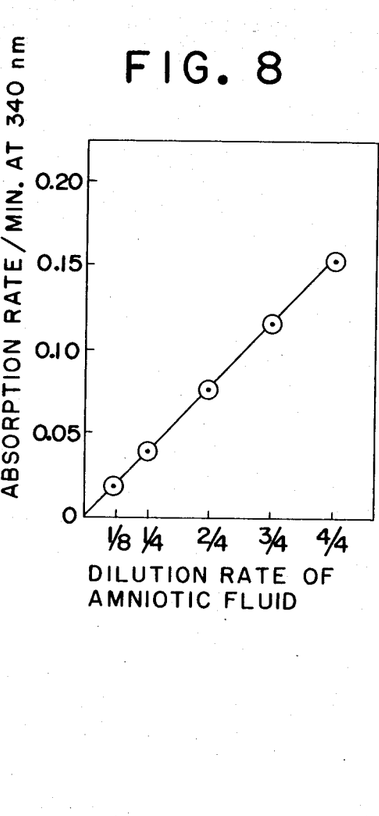
FIG. 8 is the quantitative assay curve for phosphatidyl glycerol.

Amniotic fluid (10 μ, 1⅛ dilutions, respectively) (containing phosphatidyl glycerol) was added to reaction mixture I (0.2 ml) and the mixture was incubated at 37° C. for 10 minutes. Reaction mixture II (0.8 ml) was added thereto, and the absorbency changes per minute were measured at 340 nm. The results are shown in FIG. 8.

Reaction mixture I without phospholipase C was used as a control.

Phosphatidyl glycerol in amniotic fluid could be assayed with good sensitivity. Phosphatidyl glycerol in amniotic fluid in this experiment was determined as 6.10 mg/100 ml.

Reaction mixture II without catalase can be used for assaying phosphatidyl glycerol by measuring $O_2$ with an oxygen electrode, or measuring the amount of generated $H_2O_2$ with a hydrogen peroxide electrode.

The following reaction mixture for the assay of phosphatidyl glycerol with a hydrogen peroxide electrode was also prepared:
50 mM phosphate buffer (pH 7.5)
phospholipase D (10 units/test)
10 mM $MgCl_2$
5 mM ATP
glycerokinase (2 units/test)
GPO (15 units/test)
0.25 mM reduced NAD
GPDH (8 units/test)

EXAMPLE 8

50 mM Tris-HCl buffer (pH 8.0)
0.75 mM reduced NAD
GPO (6 units/test)
GPDH (5 units/test)

Figure 9:
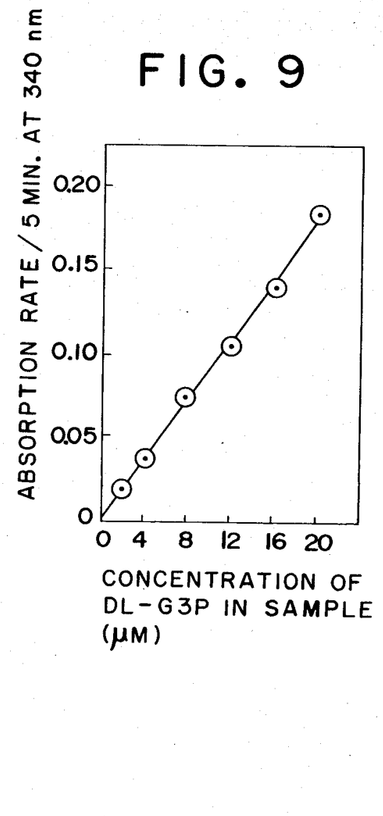
FIG. 9 is the quantitative assay curve for DL-G3P by the endpoint method.

The reaction mixture (0.5 ml) hereinabove in a small test tube was preincubated at 37° C. DL-G3P solutions (20 μl) (0, 2, 4, 8, 12, 16 and 20 μM, respectively) were added thereto and the mixtures were incubated at 37° C. for exactly 5 minutes. 1% sodium lauryl sulfate solution (2.5 ml) containing 5 mM N-ethylmaleimide was added thereto to stop the reaction. The absorbency at 340 nm was measured and corrected by comparison with a control. A good quantitative assay with linearity was obtained, as shown in FIG. 9.

Distilled water (20 μl) was added in place of DL-G3P as a control. The cycling ratio in this example was 5400/hour.

What is claimed is:

1. A quantitative assay method for a component selected from the group consisting of L-glycero-3-phosphate (G3P), dihydroxyacetone-3-phosphate (DHAP), nicotinamide adenine dinucleotide (NAD) and reduced NAD, in a specimen to be assayed, comprising causing a component in the specimen to take part in the reaction wherein GPO is glycerophosphate oxidase and GPDH is glycerophosphate dehydrogenase, and measuring a detectable change in the amount of a consumed or generated component of the reaction system.

2. An assay method according to claim 1, wherein the NAD generated in the reaction is reacted with a second dehydrogenase for substrate NAD and a substrate for the said second dehydrogenase, and the said generated NAD is used in the reaction together with the said reduced NAD.

3. An assay method according to claim 1, wherein G3P in the specimen is generated by an enzymatic reaction system comprising phosphatidyl glycerol and phospholipase C.

4. An assay method according to claim 1, wherein G3P in the specimen is generated by an enzymatic reaction system comprising adenosine triphosphate (ATP), glycerol and glycerokinase.

5. An assay method according to claim 4, wherein said glycerol is derived from an enzymatic reaction system comprising phosphatidyl glycerol and phospholipase D.

6. An assay method according to claim 4, wherein said glycerol is derived from an enzymatic reaction system comprising glyceride and lipase.

7. An assay method according to claim 4, wherein said ATP is derived from an enzymatic reaction system comprising creatine phosphate, adenosine diphosphate (ADP) and creatine kinase.

8. An assay method according to claim 4, wherein said ATP is derived from an enzymatic reaction system comprising phosphoenol pyruvate, ADP and pyruvate kinase.

9. An assay method according to claim 1, wherein said detectable change is the amount of consumed $O_2$.

10. An assay method according to claim 1, wherein said detectable change is the amount of generated $H_2O_2$.

11. An assay method according to claim 1, wherein said detectable change is the amount of consumed reduced NAD.

12. A quantitative assay method for a component selected from the group consisting of L-glycero-3-phosphate (G3P), dihydroxyacetone-3-phosphate (DHAP), nicotinamide adenine dinucleotide (NAD) and reduced NAD, in a specimen to be assayed, comprising causing a component in the specimen to take part in the reaction wherein GPO is glycerophosphate oxidase and GPDH is glycerophosphate dehydrogenase, and measuring the amount of consumed reduced NAD.

* * * * *